United States Patent [19]

Harper et al.

[11] Patent Number: 5,110,830

[45] Date of Patent: May 5, 1992

[54] BENZENESULFONAMIDES TREATMENT OF TUMORS SUSCEPTIBLE TO

[75] Inventors: Richard W. Harper, Indianapolis; Gerald A. Poore, Martinsville; Brent J. Rieder, Greenfield, all of Ind.

[73] Assignee: Eli Lilly and Company, Indianapolis, Ind.

[21] Appl. No.: 581,840

[22] Filed: Sep. 13, 1990

Related U.S. Application Data

[60] Continuation of Ser. No. 336,404, Apr. 11, 1989, abandoned, which is a division of Ser. No. 729,581, May 2, 1985, Pat. No. 4,845,128, which is a continuation-in-part of Ser. No. 625,280, Jun. 27, 1984, abandoned.

[51] Int. Cl.[5] .................... A01N 47/34; A01N 41/06; A01N 41/12
[52] U.S. Cl. .................................. 514/592; 514/602; 514/608
[58] Field of Search .................... 514/592, 602, 608

[56] References Cited

U.S. PATENT DOCUMENTS

| | | | |
|---|---|---|---|
| 2,941,884 | 6/1960 | Aeschlimann et al. | 514/592 |
| 3,483,297 | 12/1969 | Weber et al. | 514/592 |
| 4,845,128 | 7/1989 | Harper et al. | 514/592 |
| 4,849,563 | 7/1989 | Sartorelli | 514/155 |

Primary Examiner—Jerome D Goldberg
Assistant Examiner—T. J. Criares
Attorney, Agent, or Firm—Joseph A. Jones; Leroy Whitaker; Robert A. Conrad

[57] ABSTRACT

This invention provides the use of certain benzenesulfonamide derivatives in the treatment of susceptible neoplasms in mammals. Also provided are certain novel benzenesulfonamide derivatives and their pharmaceutical formulations.

8 Claims, No Drawings

BENZENESULFONAMIDES TREATMENT OF TUMORS SUSCEPTIBLE TO

BACKGROUND OF THE INVENTION

Despite the development of numerous chemical agents and sophisticated regimens of drug therapy, the ravages of cancer continue to extract an ever-increasing human toll of suffering and death. Although many advances have been made, especially in the area of combination drug therapy, the need for new and better methods of treating neoplasms and leukemias has not diminished. This is especially evident in the area of inoperable or metastatic solid tumors, such as various forms of lung cancer.

To be especially useful, new chemotherapeutic agents should have a wide spectrum of activity, a large therapeutic index, and be chemically stable and compatible with other agents. In addition, any new agents having oral activity would be especially useful so that initial treatment and subsequent maintenance therapy would be made easily and without inconvenience or pain to the patient.

We have discovered a series of sulfonylureas which are useful in the treatment of solid tumors. The compounds are orally active and relatively non-toxic providing an excellent therapeutic index. Some of the compounds and their formulations are novel.

Certain sulfonylureas used in this invention are known in the art. Compounds such as 1-(4-fluoro-, 4-chloro-, 4-bromo-, and 4-methyl-phenyl)-3-[phenyl- and (4-chloro-, 4-bromo-, and 4-methyl-phenyl-)sulfonyl-]urea are taught in Chemical Abstracts 71:11457w (1969), Holland, et al., *J. Med. Pharm. Chem.*, 3 (1), 99 (1961), Gandhi, et al., *Arzneim.-Forsch.*, 21, 968 (1971), Rajagopalan, et al., *J. Org. Chem.*, 30, 3369 (1965), and Petersen, *Chem. Ber.*, 83, 551 (1950). In general, these compounds are taught to have oral hypoglycemic activity. In addition, some antimycotic activity is noted and the compounds have also been prepared as derivatives of carbodiimides. The Holland reference also teaches the preparation of 1-(3-trifluoromethylphenyl)-3-(4-methylphenylsulfonyl)urea, although the compound is taught to be lacking hypoglycemic activity. A general review of compounds of this structural type is taught by Kurzer, *Chem. Rev.*, 50, 1 (1952). No anti-tumor activity is disclosed or inferred in any of the above references.

SUMMARY OF THE INVENTION

This invention provides a method of treating susceptible neoplasms in mammals which comprises administering to a mammal in need of such treatment an effective amount of a compound of the formula

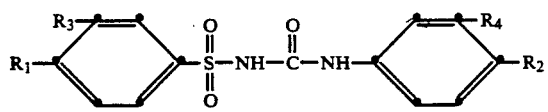

wherein:
$R_1$ and $R_3$ are independently hydrogen, $C_1$-$C_3$ alkyl, halo, trifluoromethyl, or $C_1$-$C_3$ alkoxy;
$R_2$ is halo, methyl, or trifluoromethyl; and
$R_4$ is hydrogen, halo, methyl, or trifluoromethyl.

This invention also provides novel compounds of the formula II

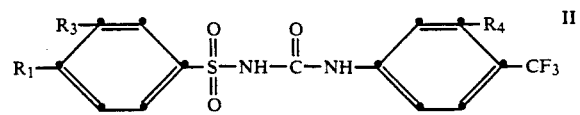

wherein $R_1$, $R_3$, and $R_4$ are the same as described above. Such compounds are especially preferred in the treatment of susceptible neoplasms in mammals and also possess hypoglycemic activity.

In addition, this invention provides pharmaceutical formulations comprising a compound of formula II in combination with a suitable pharmaceutical carrier, diluent, or excipient. These formulations are particularly useful in treating mammals suffering from susceptible neoplasms.

Also provided by this invention are pharmaceutical formulations comprising a compound of the formula

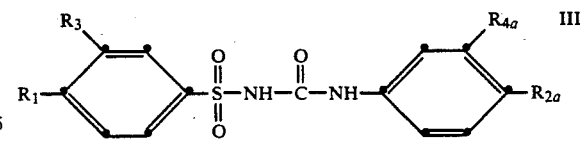

wherein $R_1$ and $R_3$ are the same as defined above and $R_{2a}$ and $R_{4a}$ are independently chloro or fluoro, in combination with a suitable pharmaceutical carrier, diluent, or excipient. These formulations are useful in the treatment of mammals suffering from susceptible neoplasms.

This invention also provides for the novel compound N-([(4-chlorophenyl)amino]carbonyl)-3-methylbenzenesulfonamide (compound IIIa). This compound is one of the most active compounds of Formula I ($R_1=R_4=$hydrogen; $R_3=$methyl; $R_2=$chloro) in the treatment of susceptible neoplasms and has virtually no hypoglycemic liability. Pharmaceutical formulations containing IIIa, such as those described above for the compounds of Formula III, are also provided.

DETAILED DESCRIPTION AND PREFERRED EMBODIMENTS

The term "halo" refers to fluoro, chloro, bromo, and iodo. The term "$C_1$-$C_3$ alkyl" refers to methyl, ethyl, propyl, and isopropyl. The term "$C_1$-$C_3$ alkoxy" refers to methoxy, ethoxy, propoxy, and isopropoxy.

The preferred compounds used in the method of this invention are those of Formula I wherein
a) $R_3$ and $R_4$ are independently chloro, fluoro, methyl, or hydrogen,
b) $R_1$ is hydrogen, halo, especially chloro, $C_1$-$C_3$ alkyl, especially methyl or ethyl, or $C_1$-$C_3$ alkoxy, especially methoxy, and
c) $R_2$ is halo, especially chloro or fluoro, or trifluoromethyl.

The especially preferred compounds used in this invention are those of formulas II and IIIa. Also especially preferred are compounds of formula I wherein $R_1$ is methyl or methoxy. The most preferred compounds are 4-methyl-N-([(4-trifluoromethylphenyl)amino]carbonyl)benzenesulfonamide, 4-methoxy-N-([(4-trifluoromethylphenyl)amino]carbonyl)benzenesulfonamide, N-([(4-chlorophenyl)amino]carbonyl)-4-methylbenzenesulfonamide, and especially N-([(4-chlorophenyl)amino]carbonyl)-3-methylbenzenesulfonamide (compound IIIa).

The compounds of formula I are generally referred to as derivatives of N-([[(substituted phenyl)amino]carbonyl)benzenesulfonamides as used in the previous paragraph. Alternatively, the compounds are referred to as 1-(substituted phenyl)-3-(optionally substituted phenylsulfonyl)ureas.

The compounds of formula I may be prepared by any number of methods known in the literature. These methods are generally summarized by Kurzer, Chem. Rev., 50, 1 (1952), especially pages 4–19. Specific references describing the preparation of compounds of formula I are those previously described in the "Background of the Invention" section above. All of the above references are expressly incorporated into this application by reference.

The preferred method of preparing the compounds of formula I is that of the reaction of a sulfonylisocyanate of the formula IV

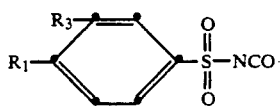   IV with an aniline derivative of the formula V

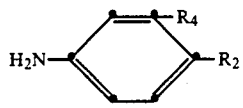   V where $R_1$, $R_2$, $R_3$, and $R_4$ are the same as previously defined.

The reaction between compounds IV and V is usually performed using equimolar amounts of the two reactants, although other ratios are operative. The reaction is best carried out in an aprotic non-reactive solvent such as benzene, toluene, acetonitrile, ether, tetrahydrofuran, dioxane, or preferably methylene chloride. The reaction may be carried out at temperatures from about 0° C. up to the boiling point of the reaction mixture. At the preferred temperature range of about 20–30° C., the reaction produces a strong exotherm and the reaction is usually complete within 1 hour. The product thus obtained is recovered by filtration and may be purified, if desired, by any number of methods known to those skilled in the art, such as chromatography or crystallization.

Alternatively, an appropriately substituted sulfonamide VI

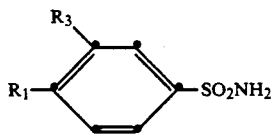   VI may be reacted with an isocyanate of the formula VII

   VII to provide the compounds of Formula I. The reaction is generally carried out in a water miscible, non-reactive solvent such as tetrahydrofuran or acetone. Generally, an equimolar amount or slight molar excess of VII is employed, although other ratios are operative. In addition, an aqueous solution of a base, such as sodium or potassium hydroxide, is employed. Usually the amount of base used is approximately equimolar to the amount of VI. The reaction is generally carried out from about 0° C. up to the boiling point of the reaction mixture. At the preferred temperature range of 20–30° C., the reaction is usually complete within about three days.

Intermediates IV, V, VI, and VII, and any intermediates required for other methods of preparation are either commercially available, are known in the literature, or can be prepared by methods known in the art.

The following examples further illustrate the preparation of the compounds of this invention. The examples are illustrative only and are not intended to limit the scope of the invention in any way.

EXAMPLE 1

4-Methyl-N-([[(4-trifluoromethylphenyl)amino]carbonyl)benzenesulfonamide

A solution of 8.0 g of 4-aminobenzotrifluoride in 10 ml of methylene chloride was added to a solution of 9.85 g of p-toluenesulfonyl isocyanate in 75 ml of methylene chloride with stirring. The mixture became quite warm and a heavy white precipitate formed. An additional 100 ml of methylene chloride were added. The reaction mixture was stirred an additional 15 minutes, and the precipitate was recovered by filtration affording 15.0 g of the title product as a white solid. A small amount of the material was crystallized from diethyl ether to provide 4-methyl-N-([[(4-trifluoromethylphenyl)amino]carbonyl)benzenesulfonamide with a melting point of 194–197° C.

Analysis for $C_{15}H_{13}F_3N_2SO_3$:
Calculated: C, 50.25; H, 3.66; N, 7.82;
Found: C, 50.02; H, 3.63; N, 7.79.

EXAMPLES 2–16

Following the general procedure of Example 1, the following compounds were prepared from the appropriate benzenesulfonyl isocyanate and aniline derivatives. Yields are expressed as percent molar yield.

2. N-([(4-chlorophenyl)amino]carbonyl)4-methylbenzenesulfonamide, 87% yield, m.p. 174–176° C.
Analysis for $C_{14}H_{13}ClN_2O_3S$:
Calculated: C, 51.77; H, 4.03; N, 8.63;
Found: C, 51.90; H, 4.08; N, 8.67.

3. 4-Methoxy-N-([[(4-trifluoromethylphenyl)amino]carbonyl)benzenesulfonamide, 58.9% yield, m.p. 188–189° C.
Analysis for $C_{15}H_{13}F_3N_2O_4S$:
Calculated: C, 48.13; H, 3.50; N, 7.48;
Found: C, 48.38; H, 3.61; N, 7.53.

4. N-([[(4-trifluoromethylphenyl)amino]carbonyl)benzenesulfonamide, 68.7% yield, m.p. 195–196° C.
Analysis for $C_{14}H_{11}F_3N_2O_3S$:
Calculated: C, 48.84; H, 3.22; N, 8.14;
Found: C, 49.09; H, 3.28; N, 8.22.

5. 4-Methyl-N-([[(4-methylphenyl)amino]carbonyl)benzenesulfonamide, 84.9% yield. m.p. 148–149° C.
Analysis for $C_{15}H_{16}N_2O_3S$:
Calculated: C, 59.19; H, 5.30; N, 9.20;
Found: C, 59.00; H, 5.21; N, 8.96.

6. 4-Bromo-N-([(4-bromophenyl)amino]carbonyl)-benzenesulfonamide, 68.0% yield, m.p. 213–215° C. with decomposition.

Analysis for $C_{13}H_{10}Br_2N_2O_3S$:
Calculated: C, 35.97; H, 2.32; N, 6.45;
Found: C, 36 21; H, 2.33; N, 6.48.

7. N-([(4-fluorophenyl)amino]carbonyl-4-methylbenzenesulfonamide, 99% yield, m.p. 172–173° C.

Analysis for $C_{14}H_{13}FN_2O_3S \cdot \tfrac{1}{2}CH_2Cl_2$ (solvate with 0.5 mole of methylene chloride):
Calculated: C, 49.65; H, 4.02; N, 7.99; S, 9.14;
Found: C, 49.84; H, 3.97; N, 8.26; S, 8.97.

8. 1-(4-Bromophenyl)-3-(4-methylbenzenesulfonyl)urea, 88% yield, m.p. 188–189° C.

Analysis for $C_{14}H_{13}BrN_2O_3S$:
Calculated: C, 45.54; H, 3.55; N, 7.59; S, 8.68;
Found: C, 45.30; H, 3.62; N, 7.49; S, 8.74.

9. N-([(4-chlorophenyl)amino]carbonyl)-4-methoxybenzenesulfonamide, 72% yield, m.p. 163–165° C.

Analysis for $C_{14}H_{13}ClN_2O_4S$:
Calculated: C, 49.34; H, 3.85; N, 8.22; S, 9.41; Cl, 10.40;
Found: C, 49.06; H, 3.75; N, 8.16; S, 9.18; Cl, 10.36.

10. N-([(4-chlorophenyl)amino]carbonyl)benzenesulfonamide, 76% yield, m.p. 180–181° C.

Analysis for $C_{13}H_{11}ClN_2O_3S$:
Calculated: C, 50.25; H, 3.57; N, 9.01; S, 10.32; Cl, 11.41;
Found: C, 50.05; H, 3.61; N, 8.92; S, 10.13; Cl, 11.21.

11. 1-(4-Chlorophenyl)-3-(4-chlorophenylsulfonyl)urea, 41.3% yield, m.p. 180–183° C.

Analysis for $C_{13}H_{10}Cl_2N_2O_3S$:
Calculated: C, 45.23; H, 2.92; N, 8.12;
Found: C, 44.95; H, 2.82; N, 8.02.

12. N-([(4-iodophenyl)amino]carbonyl)-4-methylbenzenesulfonamide, 87% yield, m.p. 197° C. with decomposition.

Analysis for $C_{14}H_{13}IN_2O_3S$:
Calculated: C, 40.04; H, 3.15; N, 6.73; S, 7.70; I, 30.49;
Found: C, 40.22; H, 3.21; N, 6.49; S, 7.47; I, 30.70.

13. N-([(4-bromophenyl)amino]carbonyl)benzenesulfonamide, 77% yield, m.p. 191–192° C.

Analysis for $C_{13}H_{11}BrN_2O_3S$:
Calculated: C, 43.96; H, 3.12; N, 7.89; S, 9.03;
Found: C, 43.76; H, 2.90; N, 7.73; S, 8.69.

14. 4-Chloro-N-([4-trifluoromethylphenyl)amino]carbonyl)benzenesulfonamide, 82.4% yield, m.p. 197–198.5° C.

Analysis for $C_{14}H_{10}ClF_3N_2O_3S$:
Calculated: C, 44.40; H, 2.66; N, 7.40; S, 8.47;
Found: C, 44.23; H, 2.47; N, 7.28; S, 8.31.

15. N-([(3,4-dichlorophenyl)amino]carbonyl)-4-methylbenzenesulfonamide, 88.4% yield, m.p. 199–200° C.

Analysis for $C_{14}H_{12}Cl_2N_2O_3S$:
Calculated: C, 46.81; H, 3.37; N, 7.80; S, 8.93;
Found: C, 46.71; H, 3.61; N, 7.59; S, 8.65.

16. 4-Chloro-N-([(4-fluorophenyl)amino]carbonyl)benzenesulfonamide, 98% yield, m.p. 201–202° C.

Analysis for $C_{13}H_{10}ClFN_2O_3S$:
Calculated: C, 47.50; H, 3.07; N, 8.52;
Found: C, 47.31; H, 3.13; N, 8.33.

EXAMPLE 17

N-([(4-Bromophenyl)amino]carbonyl)-4-methoxybenzenesulfonamide

To a solution of 9.97 g of 4-methoxybenzenesulfonamide in 54 ml of acetone were added 54 ml of a 1N sodium hydroxide solution. With stirring, a solution of 11.55 g of 4-bromophenylisocyanate in 50 ml of acetone was added. After stirring at room temperature for three days, the reaction mixture was filtered and 55 ml of 1N hydrochloric acid were added to the filtrate providing a fine white precipitate. Two hundred milliliters of water were added, and the solid was recovered by filtration to provide 18.85 g of the desired title product.

Analysis for $C_{14}H_{13}BrN_2O_4S$:
Calculated: C, 43.65; H, 3.40; N, 7.27; S, 8.32;
Found: C, 43.52; H, 3.54; N, 7.32; S, 8.31.

EXAMPLES 18–19

Following the procedure of Example 17, the following compounds were prepared from the appropriate sulfonamide and the corresponding isocyanate.

18. 3,4-Dichloro-N-([(4-trifluoromethylphenyl)amino]carbonyl)benzenesulfonamide, 86% yield.

Analysis for $C_{14}H_9Cl_2F_3N_2O_3S$:
Calculated: C, 40.70; H, 2.20; N, 6.78; S, 7.76;
Found: C, 40.70; H, 2.36; N, 6.61; S, 7.62.

19. 3-Trifluoromethyl-N-([(4-trifluoromethylphenyl)amino]carbonyl)benzenesulfonamide, 89.5% yield.

Analysis for $C_{15}H_{10}F_6N_2O_3S$:
Calculated: C, 43.70; H, 2.44; N, 6.79; S, 7.78;
Found: C, 43.80; H, 2.18; N, 6.92; S, 8.04.

EXAMPLE 20

N-([(3,4-dichlorophenyl)amino]carbonyl)benzenesulfonamide

The title compound was prepared in 83.5% yield from benzenesulfonyl isocyanate and 3,4-dichloroaniline following the procedure of Example 1, m.p. 194–195° C.

Analysis for $C_{13}H_{10}Cl_2N_2O_3S$:
Calculated: C, 45.23; H, 2.92; N, 8.12; S, 9.29;
Found: C, 45.04; H, 3.07; N, 7.82; S, 9.34.

EXAMPLES 21–31

Following the procedure of Example 17, the following compounds were prepared from the appropriate sulfonamide and the corresponding isocyanate.

21. 3,4-Dichloro-N-([(4-chlorophenyl)amino]carbonyl)benzenesulfonamide, 82% yield, m.p. 183–184° C.

Analysis for $C_{13}H_9Cl_3N_2O_3S$:
Calculated: C, 41.13; H, 2.39; N, 7.38; S, 8.45;
Found: C, 40.85; H, 2.52; N, 7.14; S, 8.56.

22. 3-Chloro-N-([(4-chlorophenyl)amino]carbonyl)benzenesulfonamide, 79% yield, m.p. 135° C.

Analysis for $C_{13}H_{10}Cl_2N_2O_3S$:
Calculated: C, 45.23; H, 2.92; N, 8.12; S, 9.29;
Found: C, 45.36; H, 2.74; N, 8.16; S, 9.51.

23. N-([(4-chlorophenyl)amino]carbonyl)-3-methylbenzenesulfonamide, 92.4% yield, m.p. 171–173° C.

Analysis for $C_{14}H_{13}ClN_2O_3S$:
Calculated: C, 51.77; H, 4.03; N, 8.63;
Found: C, 51.53; H, 4.15; N, 8.63.

24. N-([(4-chlorophenyl)amino]carbonyl)-3-methoxybenzenesulfonamide, 91% yield, m.p. 152–154° C.

Analysis for $C_{14}H_{13}ClN_2O_4S$:
Calculated: C, 49.34; H, 3.85; N, 8.22; S, 9.41;
Found: C, 49.49; H, 3.97; N, 8.06; S, 9.22.

25. N-([(4-chlorophenyl)amino]carbonyl)-3,4-dimethylbenzenesulfonamide, 82.9% yield, m.p. 149–151° C.

Analysis for $C_{15}H_{15}ClN_2O_3S$:
Calculated: C, 53.18; H, 4.46; N, 8.27; S, 9.46;

Found: C, 53.44; H, 4.33; N, 8.03; S, 9.24.

26. N-([(4-chlorophenyl)amino]carbonyl)-4-ethylbenzenesulfonamide, 85.4% yield, m.p. 176–177° C.

Analysis for $C_{15}H_{15}ClN_2O_3S$:
Calculated: C, 53.18; H, 4.46; N, 8.27;
Found: C, 53.04; H, 4.56; N, 8.13.

27. N-([(4-chlorophenyl)amino]carbonyl)-4-ethoxybenzenesulfonamide, 65% yield, m.p. 172–174° C.

Analysis for $C_{15}H_{15}ClN_2O_4S$:
Calculated: C, 50.78; H, 4.26; N, 7.90; S, 9.04;
Found C, 50.75; H, 4.23; N, 7.86; S, 9.06.

28. N-([(4-chlorophenyl)amino]carbonyl)-4-fluorobenzenesulfonamide, 67% yield.

Analysis for $C_{13}H_{10}ClFN_2O_3S$:
Calculated: C, 47.50; H, 3.07; N, 8.52; Cl, 10.78; F, 5.78;
Found: C, 47.45; H, 3.25; N, 8.44; Cl, 11.02; F, 6.06.

29. N-([(4-chlorophenyl)amino]carbonyl)-3,4-diethylbenzenesulfonamide, 87% yield, m.p. 108–111° C.

Analysis for $C_{17}H_{19}ClN_2O_3S$:
Calculated: C, 55.66; H, 5.22; N, 7.64; S, 8,74;
Found: C, 55.69; H, 5.13; N, 7.70; S, 8.57.

30. N-([(4-chlorophenyl)amino]carbonyl)-4-propylbenzenesulfonamide, 79% yield, m.p. 125° C.

Analysis for $C_{16}H_{17}ClN_2O_3S$:
Calculated: C, 54.47; H, 4.86; N, 7.94; S, 9.09;
Found: C, 54.71; H, 5.00; N, 7.66; S, 9.34.

31. N-([(4-chlorophenyl)amino]carbonyl)-4-(1-methylethyl)benzenesulfonamide, 89% yield, m.p. 175–178° C.

Analysis for $C_{16}H_{17}ClN_2O_3S$:
Calculated: C, 54.47; H, 4.86; N, 7.94; S, 9.09;
Found: C, 54.23; H, 4.75; N, 7.86; S, 8.85.

EXAMPLE 32

4-Chloro-N-([(3,4-dichlorophenyl)amino]carbonyl)benzenesulfonamide

Following the procedure of Example 1, 5.04 g of 4-chlorobenzenesulfonyl isocyanate and 3.85 g of 3,4-dichloroaniline were allowed to react providing 8.06 g of the desired title product, m.p. 195–196° C.

Analysis for $C_{23}H_9Cl_3N_2O_3S$:
Calculated: C, 41.13; H, 2.39; N, 7.38; S, 8.45;
Found: C, 40.92; H, 2.60; N, 7.12; S, 8.32.

EXAMPLE 33

N-([(4-bromo-3-methylphenyl)amino]carbonyl-4-methylbenzenesulfonamide

A solution of 5.58 g of 4-bromo-3-methylaniline in 20 ml of toluene and 5 ml of methylene chloride was added to a solution of 5.91 g of p-toluenesulfonyl isocyanate in 50 ml of toluene and 10 ml of methylene chloride under a nitrogen atmosphere. The mixture was stirred overnight and filtered, providing 9.19 g of the title product, m.p. 178–180° C.

Analysis for $C_{15}H_{15}BrN_2O_3S$:
Calculated: C, 47.01; H, 3.95; N, 7.31; S, 8.37;
Found C, 46.92; H, 4.04; N, 7.39; S, 8.54.

The compounds of formula I have been shown to be active against transplanted mouse tumors in vivo. The compounds are active when administered orally or by the intraperitoneal route. The compounds are active in the test systems when administered according to a variety of dosage schedules. In general, the compounds were administered daily or twice daily for 8–10 days, or on days 1, 5, and 9 after inoculation with the appropriate tumor. In some additional tests, the compounds were active even though not administered until several days after inoculation with the tumor.

To demonstrate the anti-tumor activity of the compounds of Formula I, the compounds were tested in animals bearing a 6C3HED lymphosarcoma, also known as the Gardner lymphosarcoma (GLS). Table 1 gives the results of several experiments in mice bearing this tumor. In the table, column 1 gives the example number of the compound; column 2, the method of administration; column 3, the dose level or dose level range and number of days this dosage was administered; and column 4, the percent inhibition of tumor growth. The results are compilations of one or more such tests which were performed with suitable control groups.

TABLE 1

| Activity of the Compounds of Formula I Against the 6C3HED Lymphosarcoma* | | | |
|---|---|---|---|
| Compound of Example No. | Route | mg/kg × days** | Percent Inhibition |
| 1 | IP | 100–200 (days 1,5,9) | 31–49 |
|   |    | 50–150 × 8–10 | 41–92 |
|   | PO | 6.25–50 (twice daily) × 8 | 28–84 |
|   |    | 25–200 × 8–10 | 28–100 |
| 2 | PO | 37.5–400 × 8 | 25–100 |
| 3 | PO | 100–200 × 8 | 86–100 |
| 4 | PO | 150 × 8 | 81–85 |
| 5 | PO | 150–600 × 8 | 31–100 |
| 6 | PO | 37.5–150 × 8 | 76–100 |
| 7 | PO | 100–1200 × 8 | 41–95 |
| 8 | PO | 37.5–200 × 8 | 59–100 |
| 9 | PO | 150 × 8 | 100 |
| 10 | PO | 100–200 × 8 | 82–100 |
| 11 | PO | 37.5–200 × 8 | 82–100 |
| 12 | PO | 150 × 8 | 76 |
| 13 | PO | 150 × 8 | 82 |
| 14 | PO | 150 × 8 | 94 |
| 15 | PO | 150–300 × 8 | 93–100 |
| 16 | PO | 150–300 × 8 | 34–74 |
| 17 | PO | 150 × 8 | 99 |
| 18 | PO | 150 × 8 | 85 |
| 19 | PO | 150 × 8 | 39 |
| 20 | PO | 50–150 × 8 | 84–100 |
| 21 | PO | 150–300 × 8 | 100 |
| 22 | PO | 150 × 8 | 98 |
| 23 | PO | 37.5–300 × 8 | 30–100 |
| 24 | PO | 150–300 × 8 | 94–100 |
| 25 | PO | 150–300 × 8 | 90–100 |
| 26 | PO | 37.5–200 × 8 | 48–100 |
| 27 | PO | 150–300 × 8 | 82–100 |
| 28 | PO | 150 × 8 | 79 |
| 29 | PO | 150–300 × 8 | 22–46 |
| 30 | PO | 150–300 × 8 | 40–70 |
| 31 | PO | 150–300 × 8 | 43–65 |
| 32 | PO | 150 × 8 | 85 |
| 33 | PO | 150–300 × 8 | 65–81 |

*Tested in male C3H mice.
**Administered in emulphor. Dosing began the day following inoculation. Compounds were dosed once every day, except where noted.

In addition, certain of the compounds of Formula I were tested in additional test systems. These include the subcutaneous B-16 melanoma (B16-sc), the Yoshida rat sarcoma (Yoshida), the X5563 plasma cell myeloma (X5563), the M-5 ovarian carcinoma (M-5), the C3H mammary carcinoma (C3H), colon carcinoma-26 (C6), the CA-755 adenocarcinoma (CA755), the P1534J lymphatic leukemia (P1534J), the P388 lymphocytic leukemia (P388), and the Lewis Lung carcinoma (LL). A summary of these test results is provided in Table 2.

TABLE 2

Activity of Compounds of Formula I against a variety of tumor models

| Compound of Example No. | Tumor | Route | mg/kg × days* | Percent Inhibition |
|---|---|---|---|---|
| 1 | B16-sc | PO | 50–150 × 10 | 24–57 |
|  | C3H | PO | 50–150 × 10 | 47–93 |
|  | CA755 | IP | 25–50 (twice daily) × 10 | 85–90 |
|  |  | PO | 75–150 × 10 | 44–94 |
|  | C6 | IP | 50–100 × 10 (5 day delay) | 42–82 |
|  |  | PO | 75–200 × 10 | 41–89 |
|  | LL | PO | 50–150 × 10 | 49–67 |
|  | M-5 | IP | 100–150 × 10 (5 day delay) | 58–83 |
|  |  | PO | 50–100 × 10 (5 day delay) | 79–93 |
|  | P1534J | IP | 50–150 × 10 | 70–96 |
|  |  | PO | 6.25–50 (twice daily) × 10 | 26–98 |
|  | X5563 | IP | 100 × 10 | 64 |
|  |  | PO | 100–150 × 10 | 62–77 |
|  | Yoshida | PO | 25–100 × 10 | 37–85 |
|  | P388 | IP | 50–150 × 10 | 15–47** |
|  |  | PO | 75–150 × 10 | 27–61** |
| 2 | M-5 | PO | 50–200 × 10 (3 day delay) | 47–99 |
|  | C6 | PO | 50–200 × 10 (3 day delay) | 60–93 |
|  | CA755 | PO | 50–200 × 10 | 69–98 |
|  | B16-sc | PO | 50–200 × 10 | 40–74 |
|  | Yoshida | PO | 50–200 × 10 | 47–85 |
|  | X5563 | PO | 50–100 × 10 | 78–91 |
|  | P388 | PO | 100–200 × 10 | 19–23** |
|  | P1534J | PO | 50–200 × 10 | 79–100 |
| 23 | CA755 | PO | 18.75–150 (twice daily) × 10 | 22–100 |
|  | LL | PO | 75–150 (twice daily) × 10 | 22–56 |
|  | C6 | PO | 37.5–75 (twice daily) × 10 | 36–76 |
|  | M-5 | PO | 18.75–75 (twice daily) × 10 | 49–90 |

*Administered in emulphor. Dosing began the day following inoculation, except where noted. Compounds were dosed once every day, except where noted.
**percent increase in survival time.

The compounds of Formula I are antineoplastic agents and the invention provides a method of treating susceptible neoplasms. The method comprises administering a compound by various routes including the oral, rectal, transdermal, subcutaneous, intravenous, intramuscular, or intranasal routes, being usually employed in the form of a pharmaceutical composition. It is a special feature of these compounds that they are effective following oral administration. Such compositions are prepared in a manner well known in the pharmaceutical art and comprise at least one active compound. Accordingly, in addition to the novel compounds of Formula II, the invention also includes pharmaceutical compositions comprising as active ingredient a compound of Formula II, III, or IIIa associated with a pharmaceutically acceptable carrier.

In making the compositions of the present invention, as well as compositions containing other compounds of Formula I, the active ingredient will usually be mixed with a carrier, or diluted by a carrier, or enclosed within a carrier which may be in the form of a capsule, sachet, paper or other container When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range. For example, dosages per day will normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active compounds any of the compounds of Formulas II, III and IIIa. The examples are illustrative only and are not intended to limit the scope of the invention in any way.

EXAMPLE 34

Hard gelatin capsules are prepared using the following ingredients:

|  | Quantity (mg/capsule) |
|---|---|
| 4-Methyl-N-([(4-trifluoromethylphenyl)amino]carbonyl)benzenesulfonamide | 250 |
| Starch dried | 200 |
| Magnesium stearate | 10 |

The above ingredients are mixed and filled into hard gelatin capsules in 460 mg quantities.

EXAMPLE 35

A tablet formula is prepared using the ingredients below:

|  | Quantity (mg/tablet) |
|---|---|
| 4-Methoxy-N-([[(4-trifluoromethylphenyl)amino]carbonyl)benzenesulfonamide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 36

An aerosol solution is prepared containing the following components:

|  | Weight % |
|---|---|
| 4-Chloro-N-([[(3-chloro-4-trifluoromethylphenyl)amino]carbonyl)benzenesulfonamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 37

Tablets each containing 60 mg of active ingredient are made up as follows:

|  |  |
|---|---|
| N-([[(3,4-dichlorophenyl)amino]carbonyl)-4-methylbenzenesulfonamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 38

Capsules each containing 80 mg of medicament are made as follows:

|  |  |
|---|---|
| N-([[(4-trifluoromethylphenyl)amino]carbonyl)benzenesulfonamide | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 39

Suppositories each containing 225 mg of active ingredient are made as follows:

|  |  |
|---|---|
| 4-Chloro-N-([[(4-trifluoromethylphenyl)amino]carbonyl)-benzenesulfonamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 40

Suspensions each containing 50 mg of medicament per 5 ml dose are made as follows:

|  |  |
|---|---|
| 4-Methyl-N-([[(3,4-difluorophenyl)amino]carbonyl)-benzenesulfonamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 41

Capsules each containing 150 mg of medicament are made as follows:

|  |  |
|---|---|
| N-([[(4-chlorophenyl)amino]carbonyl)-3-methylbenzenesulfonamide | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.
  We claim:

1. A method of treating susceptible neoplasms in mammals which comprises administering to a mammal in need of said treatment an effective amount of a compound of the formula

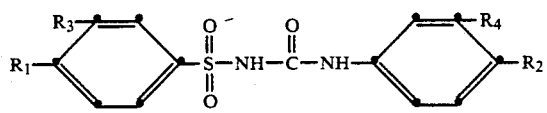

wherein:
$R_1$ and $R_3$ are independently hydrogen, $C_1$–$C_3$ alkyl, halo, trifluoromethyl, or $C_1$–$C_3$ alkoxy;
$R_2$ is halo, methyl, or trifluoromethyl; and
$R_4$ is hydrogen, halo, methyl, or trifluoromethyl.

2. The method of claim 1 employing a compound wherein $R_4$ is hydrogen.

3. The method of claim 2 employing a compound wherein $R_3$ is hydrogen.

4. The method according to claim 3 employing 4-methyl-N-([(4-trifluoromethylphenyl)amino]carbonyl)-benzenesulfonamide.

5. The method according to claim 3 employing N-([(4-chlorophenyl)amino]carbonyl)-4-methylbenzenesulfonamide.

6. The method according to claim 3 employing 4-methoxy-N-([(4-trifluoromethylphenyl)amino]carbonyl)benzenesulfonamide.

7. The method according to claim 3 employing 4-chloro-N-([(4-trifluoromethylphenyl)amino]carbonyl)-benzenesulfonamide.

8. The method according to claim 2 employing N-([(4-chlorophenyl)amino]carbonyl)-3-methylbenzenesulfonamide.

* * * * *